United States Patent
Bombardelli et al.

(10) Patent No.: US 8,226,994 B2
(45) Date of Patent: Jul. 24, 2012

(54) FORMULATIONS WITH SANGUINARINE, CHELERYTHRINE OR CHELIDONINE FOR THE TREATMENT OF WARTS, VERRUCAS AND PSORIATIC PLAQUES

(75) Inventors: Ezio Bombardelli, Groppello Cairoli (IT); Gabriele Fontana, Milan (IT); Paolo Morazzoni, Milan (IT); Antonella Riva, Milan (IT); Massimo Ronchi, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 12/921,476

(22) PCT Filed: Mar. 9, 2009

(86) PCT No.: PCT/EP2009/001672
§ 371 (c)(1),
(2), (4) Date: Sep. 8, 2010

(87) PCT Pub. No.: WO2009/112226
PCT Pub. Date: Sep. 17, 2009

(65) Prior Publication Data
US 2011/0014306 A1  Jan. 20, 2011

(30) Foreign Application Priority Data
Mar. 10, 2008  (IT) .............................. MI2008A0395

(51) Int. Cl.
*A61K 36/28*  (2006.01)
*A61K 31/435*  (2006.01)
*A61P 17/12*  (2006.01)

(52) U.S. Cl. ........ 424/737; 424/749; 514/279; 514/280; 514/863

(58) Field of Classification Search ........................ None
See application file for complete search history.

(56) References Cited

U.S. PATENT DOCUMENTS 4,590,061 A * 5/1986 Southard .................. 424/9.71
2002/0150630 A1 * 10/2002 Brooks et al. .............. 424/643
2003/0099726 A1 * 5/2003 Squires ..................... 424/725

FOREIGN PATENT DOCUMENTS

| DE | 102005060182 A1 * | 6/2007 |
| EP | 565495 A1 * | 10/1993 |
| EP | 1774955 A2 * | 4/2007 |
| FR | 2 661 330 | 10/1991 |
| FR | 2 710 266 | 3/1995 |
| WO | WO 2008012666 A2 * | 1/2008 |

OTHER PUBLICATIONS http://www.healthinplainenglish.com/health/skin/psoriasis/. Health in Plain English: "Psoriasis". Downloaded from world wide web Sep. 11, 2011.*
http://hdl.handle.net/123456789/7003. Sapprasert, Piyaluk. Local anesthetic effect of pellitorine, an active compound isolated from Cha-plu fruit (Piper sarmentosum Roxb.), 2003. Chulalongkurn University Intellectual Repository. Downloaded from world wide web on Sep. 21, 2011.*
Database WPI week 198648, Thomson Scientific, London, GB 1986-313850.
King, M. et al. "Oral squamous cell carcinoma proliferative phenotype is modulated by proanthocyanidins: a potential prevention and treatment alternative for oral cancer" BMC Complementary and Alternative Medicine, vol. 7, No. 1, Jun. 19, 2007, p. 22.

* cited by examiner

*Primary Examiner* — Michele Flood
(74) *Attorney, Agent, or Firm* — Lucas & Mercanti, LLP

(57) ABSTRACT

The invention provides formulations containing sanguinarine, chelerythrine or chelidonine or their salts or extracts containing them, mixed with suitable vehicles and/or excipients, for the treatment of common skin warts and verrucas, anal and vulvar warts and psoriatic plaques.

15 Claims, No Drawings

FORMULATIONS WITH SANGUINARINE, CHELERYTHRINE OR CHELIDONINE FOR THE TREATMENT OF WARTS, VERRUCAS AND PSORIATIC PLAQUES

This application is a U.S. national stage of PCT/EP2009/001672 filed on Mar. 9, 2009 which claims priority to and the benefit of Italian Application No. MI2008A000395 filed on Mar. 10, 2008, the contents of which are incorporated herein by reference.

SUMMARY

The present invention relates to pharmaceutical formulations useful in the treatment of common skin warts and verrucas, anal and vulvar warts and psoriatic plaques.

The formulations of the invention contain free or salified benzophenanthridine alkaloids and suitable vehicles, depending on the area to be treated. Said alkaloids possess a potent antiproliferative, antibacterial, antifungal, analgesic, antiangiogenic and anti-inflammatory action which makes them useful for the treatment of warts, verrucas and psoriasis.

Vegetable oils rich in polyunsaturated acids are used as vehicles to facilitate the absorption of alkaloids.

TECHNICAL BACKGROUND

Warts and verrucas are the result of infections of the epithelia of the skin and mucous membranes by human papillomavirus and cytomegalovirus, and can be considered as neoplasms. These infections can be associated with a wide variety of benign and malignant tumours, and therefore require suitable treatment. Warts, depending on the type of infecting virus, are usually present in all parts of the body, on the hands and face, and especially in the anogenital region. Anogenital warts usually invade the skin and the proximal mucosa. In circumcised men and male homosexuals, the glans and urethral meatus are also involved. In women, these warts can degenerate to fibroepitheliomas and a variety of benign or malignant mucocutaneous tumours. In many cases the complications of warts include severe itching, occasional bleeding, and often bacterial and fungal infections. Another widespread form of warts affects elderly people; these warts are located on the face, neck and chest, causing an unsightly appearance and functional impairment.

Patients who suffer from warts and verrucas often develop anxiety and depression. The current treatments for this disorder, which are not always completely effective, involve the use of viral antimetabolites such as 5-fluorouracyl, or products like podophyllotoxin and interferon, applied topically and systemically, with mediocre results. A tea extract for the treatment of warts and verrucas, requiring topical application for months, was recently approved in the United States of America. The first-line treatment for external warts and verrucas is still surgical, involving ablation of the removable mass and repetition of the treatment several times to ensure thorough eradication. Several months is an unacceptably long time to eradicate the disease, bearing in mind how contagious it is.

The first-line treatment for psoriatic plaques generally consists of using products with a keratolytic and emollient action which, however, do not cure the problem. The use of corticosteroids is not generally recommended because of their known side effects.

One of the plants which has been most widely studied is *Sanguinaria canadensis*, already used by native Americans to treat tumours and skin sores. Numerous alkaloids, such as sanguinarine, chelerythrine, chelidonine and other minor ones, which are also common in other Papaveraceae, have been isolated from this plant, especially its roots.

All these plants have been studied since the beginning of this century in view of their use as medicinal plants in folk medicine. Yellow latex of *Chelidonium majus* was used in the past to treat warts, verrucas and benign skin tumours; however, its use has long been discontinued because of significant tolerability problems. The most widespread use of these alkaloids, especially chelidonine, was to treat infectious diseases such as tuberculosis, or protozoa such as leishmaniasis and malaria; however, their systemic toxicity prevented their long-term use.

The use of benzophenanthridine alkaloids or salts thereof for the preparation of medicaments for the treatment of tumours is disclosed in Italian patent application no. MI2008A284, filed on 20 Feb. 2008 by the same Applicant. The use of benzophenanthridine alkaloids chosen from sanguinarine, chelerythrine or chelidonine is disclosed in particular.

Italian patent application no. MI2008A38, filed on 11 Jan. 2008 by the same Applicant, describes formulations containing sanguinarine or chelerythrine, or their salts or extracts containing them, for the treatment and prevention of mucositis, especially mucositis induced by chemotherapy, radiotherapy or immunosuppressant treatment.

DESCRIPTION OF THE INVENTION

It has now surprisingly been found that the benzophenanthridine alkaloids sanguinarine, chelerythrine and chelidonine, in free or salified form, can be used advantageously to treat common skin warts and verrucas (including those typical of elderly people), anal and vulvar warts, and psoriatic plaques.

The invention therefore provides formulations containing sanguinarine, chelerythrine or chelidonine or their salts or extracts containing them, mixed with suitable vehicles and/or excipients, for the treatment of common skin warts and verrucas, anal and vulvar warts, and psoriatic plaques.

Sanguinarine, chelerythrine and chelidonine may be present in substantially pure form or in the form of extracts of *Sanguinaria canadensis, Macleaya cordata* or *Macleaya macrocarpa*, or *Chelidonium majus*.

The invention also relates to the use of sanguinarine, chelerythrine or chelidonine, or salts or extracts containing them, for the preparation of medicaments for the treatment of common skin warts and verrucas, anal and vulvar warts, and psoriatic plaques.

The formulations according to the invention, administered by locoregional application, rapidly eliminate warts, verrucas and psoriatic plaques, without irritating the surrounding tissue. The treatments cure the disease in less than a month, without causing side effects which require the discontinuance of the treatment.

It has also been found that the salts of these alkaloids with luteic acid are particularly effective for the purposes of this invention. Said salts are prepared by reacting the sulphates or chlorides of the alkaloids with luteic acid sodium or potassium salt, and subsequent crystallisation.

The formulations of the invention can also contain procyanidins, as such or in the form of extracts containing them, to strengthen the antiviral activity.

According to a preferred aspect, therefore, the formulations of the invention may contain procyanidolic compounds, in particular extract of *Vitis vinifera* and procyanidin A2, B2 and B6. According to a particularly preferred aspect, the formulations of the invention will be combined with proanthocyanidin A2.

Moreover, as of warts, verrucas and psoriasis often cause itching, the alkaloids according to the invention can be combined with isobutylamides of polyunsaturated acids or extracts containing them, which reduce peripheral pain and itching due to their ability to bind cannabinoid CB1 and CB2 receptors. The combination of alkaloids with isobutylamides operates synergically by eliminating the warts and verrucas, inflammation in the area affected by the virus, and itching, which in some cases makes social life difficult.

Consequently, according to a further preferred aspect, the formulations of the invention may also contain a lipophilic extract of *Zanthoxylum bungeanum* or *Echinacea angustifolia*, or single isobutylamides such as pellitorine.

According to a preferred aspect, the formulations of the invention will preferably contain sanguinarine, chelerythrine or chelidonine, in free or salified form, in quantities ranging between 0.1 mg and 1 mg per square centimetre of human skin.

According to a preferred aspect, the formulations of the invention will preferably contain between 0.01 mg and 0.1 mg of said isobutylamides, as such or in the form of extracts containing them.

According to a preferred aspect, the formulations of the invention may be formulated in water/oil emulsions or in oils rich in polyunsaturated fatty acids, particularly ω-3, such as the oils of *Enothera biennis, Linum usatissimum, Ribes nigrum* and the like, which increase the tissue and cell permeation of the active constituents.

The formulations of the invention can be prepared according to well-known conventional methods, such as those described in "Remington's Pharmaceutical Handbook", Mack Publishing Co., N.Y., USA, together with suitable excipients. Examples of formulations according to the invention include creams, ointments, powders, lotions and the like.

For internal warts, the compounds according to the invention can be formulated as vaginal pessaries or suppositories or equivalent formulations for vaginal or anal treatment, including capsules that dissolve at internal body temperature.

For the treatment of psoriasis with keratinised plaques, the formulations will be based on excipients that keep the affected area moisturised.

The examples set out below illustrate the invention.

EXAMPLE 1

Oily Suspension for Soft Gelatin Capsules Designed to be Inserted in the Vaginal Meatus

| | |
|---|---|
| *Macleaya cordata* lipophilic extract (75%) | 15 mg |
| Procyanidin A2 | 20 mg |
| *Echinacea angustifolia* isobutylamides | 0.5 mg |
| Soya lecithin | 50 mg |
| Beeswax | 50 mg |
| Vegetable oil q.s. for | 800 mg |

EXAMPLE 2

Cream (Oil-in-Water Emulsion)

| | |
|---|---|
| Chelidonine luteate | 200.00 mg |
| Procyanidin A2 | 400.00 mg |
| *Zanthoxylum bungeanum* lipophilic extract | 200.00 mg |
| Propylene glycol | 10.00 g |
| Isopropyl myristate | 5.00 g |
| Cetyl alcohol | 5.00 g |
| Polysorbate | 3.00 g |
| Carbomer | 0.40 g |
| Methyl p-hydroxybenzoate | 0.10 g |
| Propyl p-hydroxybenzoate | 0.05 g |
| Purified water q.s. for | 100 g |

EXAMPLE 3

Vaginal Pessary

| | |
|---|---|
| *Macleaya* alkaloid fraction | 3.0 mg |
| Proanthocyanidin A2 | 20.0 mg |
| *Echinacea angustifolia* isobutylamides | 0.5 mg |
| Glycerides of fatty acids q.s. for | 2.0 g |

EXAMPLE 4

Psoriasis Ointment

| | |
|---|---|
| *Macleaya* alkaloid fraction | 300.00 mg |
| *Vitis vinifera* total procyanidins | 300.00 mg |
| Propylene glycol | 10.00 g |
| Isopropyl myristate | 3.00 g |
| *Enothera biennis* oil | 2.00 g |
| Cetyl alcohol | 5.00 g |
| Polysorbate | 3.00 g |
| Carbomer | 0.40 g |
| Methyl p-hydroxybenzoate | 0.10 g |
| Propyl p-hydroxybenzoate | 0.05 g |
| Purified water q.s. for | 100.00 g |

The invention claimed is:

1. A formulation comprising luteic acid salts of sanguinarine, chelerythrine or chelidonine mixed with suitable vehicles and/or excipients for the treatment of common skin warts, verrucas, anal warts, vulvar warts and psoriatic plaques.

2. The formulation as claimed in claim 1, comprising luteic acid salts of sanguinarine.

3. The formulation as claimed in claim 1, comprising luteic acid salts of chelerythrine.

4. The formulation as claimed in claim 1, comprising luteic acid salts of chelidonine.

5. The formulation as claimed in claim 1 further comprising procyanidolic compounds selected from the group consisting of consisting of procyanidin A2, procyanidin B2, procyanidin B6, and proanthocyanidin A2.

6. The formulation as claimed in claim 1, comprising proanthocyanidin A2.

7. The formulation as claimed in claim 1 further comprising an effective amount of natural or synthetic isobutylamides.

8. The formulation as claimed in claim 7, wherein the isobutylamides are contained in a lipophilic extract of *Zanthoxylum bungeanum* or a lipophilic extract of *Echinacea angustifolia*.

9. The formulation as claimed in claim 7, wherein the isobutylamides consist of pellitorine.

10. The formulation as claimed in 1, wherein the formulation is in the form of a cream, an ointment, a powder, a lotion, a vaginal pessary, a suppository, and a capsule that dissolves at internal body temperature.

11. A method of treating common skin warts, verrucas, anal warts, vulvar warts and psoriatic plaques in a patient comprising preparing a medicament comprising luteic acid salts of sanguinarine, chelerythrine or chelidonine and administering an effective amount of the medicament to a patient in need thereof.

12. The method as claimed in claim 11, wherein the medicament further comprises procyanidolic compounds selected from the group consisting of procyanidin A2, procyanidin B2, procyanidin B6, and proanthocyanidin A2.

13. The method as claimed in claim 11, wherein the medicament further comprises an effective amount of natural or synthetic isobutylamides.

14. The formulation as claimed in claim 7, wherein the effective amount ranges between 0.01 mg and 0.1 mg of the isobutylamides.

15. The method as claimed in claim 13, wherein the effective amount ranges between 0.01 mg and 0.1 mg of the isobutylamides.

* * * * *